US012751485B2

(12) United States Patent
Renner et al.

(10) Patent No.: US 12,751,485 B2
(45) Date of Patent: Oct. 6, 2026

(54) EVAPORATOR DEVICE FOR AN INHALER, AND METHOD FOR PRODUCING AN INHALER

(71) Applicant: KÖRBER TECHNOLOGIES GMBH, Hamburg (DE)

(72) Inventors: Johann Renner, Oy-Mittelberg (DE); Till Huesgen, Burgberg (DE)

(73) Assignee: Nicoventures Trading Limited, London (GB)

( * ) Notice: Subject to any disclaimer, the term of this patent is extended or adjusted under 35 U.S.C. 154(b) by 510 days.

(21) Appl. No.: 18/033,667

(22) PCT Filed: Oct. 26, 2021

(86) PCT No.: PCT/EP2021/079671
§ 371 (c)(1),
(2) Date: Apr. 25, 2023

(87) PCT Pub. No.: WO2022/090220
PCT Pub. Date: May 5, 2022

(65) Prior Publication Data

US 2023/0320417 A1 Oct. 12, 2023

(30) Foreign Application Priority Data

Oct. 27, 2020 (DE) ..................... 10 2020 128 184.6

(51) Int. Cl.
*A24F 40/10* (2020.01)
*A24F 40/44* (2020.01)
(Continued)

(52) U.S. Cl.
CPC .............. *A24F 40/10* (2020.01); *A24F 40/44* (2020.01); *A24F 40/46* (2020.01); *A61M 11/041* (2013.01);
(Continued)

(58) Field of Classification Search
None
See application file for complete search history.

(56) References Cited

U.S. PATENT DOCUMENTS

2011/0155153 A1* 6/2011 Thorens .................. A24F 40/46 131/329
2014/0069424 A1* 3/2014 Poston .................. A61M 15/06 128/202.21
(Continued)

FOREIGN PATENT DOCUMENTS

CN 109924547 A 6/2019
CN 111107759 A 5/2020
(Continued)

OTHER PUBLICATIONS

Examination Report issued by the German Patent Office with respect to the German priority application No. 10 2020 128 184.6, 6 pages.

*Primary Examiner* — Linda L Gray
(74) *Attorney, Agent, or Firm* — SALIWANCHIK, LLOYD & EISENSCHENK

(57) ABSTRACT

A vaporizer device for an inhaler, such as for an electronic cigarette product or a medical inhaler, can include: a vaporizer film, which in turn comprises a layer system with a polymer film and at least one metal film which contacts the polymer film over its surface and is designed as a heating element; a liquid reservoir; and a wick structure, which is configured to supply the vaporizer film with liquid from the liquid. The vaporizer film can include at least one first receiving opening for receiving liquid and at least one dispensing opening for dispensing vaporized liquid. The vaporizer film is in contact with the wick structure via the base surface, and the vaporizer film forms at least one supply
(Continued)

channel, via which the at least one first receiving opening can be supplied with liquid from the wick structure.

21 Claims, 7 Drawing Sheets

(51) Int. Cl.
*A24F 40/46* (2020.01)
*A61M 11/04* (2006.01)

(52) U.S. Cl.
CPC ..... *A61M 2202/04* (2013.01); *A61M 2207/10* (2013.01)

(56) References Cited

U.S. PATENT DOCUMENTS

| | | | | |
|---|---|---|---|---|
| 2019/0104764 | A1 | 4/2019 | Tucker et al. | |
| 2019/0183180 | A1 | 6/2019 | Rath et al. | |
| 2020/0037662 | A1 * | 2/2020 | Richmond | H05B 1/0227 |
| 2021/0235760 | A1 * | 8/2021 | Lauenstein | A61M 15/06 |
| 2024/0090089 | A1 * | 3/2024 | Tucker | A24F 40/70 |

FOREIGN PATENT DOCUMENTS

| | | | |
|---|---|---|---|
| CN | 111227315 | A | 6/2020 |
| CN | 111772242 | A | 10/2020 |
| DE | 10 2016 120 803 | A1 | 5/2018 |
| DE | 10 2017 130 501 | A1 | 6/2019 |
| EP | 1918668 | A1 | 5/2008 |
| EP | 3 099 190 | B1 | 11/2018 |
| EP | 2 850 956 | B1 | 6/2019 |
| EP | 3 282 872 | B1 | 8/2019 |
| WO | WO 2016/166670 | A1 | 10/2016 |
| WO | WO 2019/211311 | A1 | 11/2019 |

* cited by examiner

EVAPORATOR DEVICE FOR AN INHALER, AND METHOD FOR PRODUCING AN INHALER

CROSS REFERENCE TO RELATED APPLICATIONS

This application is a National Stage Application of International Application Number PCT/EP2021/079671, filed Oct. 26, 2021; which claims priority to German Patent Application No. 10 2020 128 184.6, filed Oct. 27, 2020.

FIELD OF INVENTION

The present invention relates to a vaporizer device for an inhaler, in particular for an electronic cigarette product or a medical inhaler, comprising a vaporizer film, which in turn comprises a layer system with a polymer film and at least one metal film which makes surface contact with the polymer film and is designed as a heating element, a liquid reservoir and a wick structure which is configured to supply the vaporizer film with liquid from the liquid reservoir, wherein the vaporizer film comprises at least one first receiving opening for receiving liquid and at least one dispensing opening for dispensing vaporized liquid, wherein the vaporizer film is in contact with the wick structure via a base surface. Furthermore, the invention relates to a method for manufacturing a vaporizer device.

BACKGROUND OF THE INVENTION

It is well known to use vaporizer heads based on the wick-coil principle in electronic cigarettes. In addition to the widely used wick-coil e-cigarettes, other approaches include the areal vaporization of liquid directly on the liquid surface; this principle is known, for example, from patent application DE 10 2016 120 803.

Furthermore, it is known from DE 10 2017 130 501 A1 to use a so-called foil vaporizer. Here, a carrier consisting of a layer system with a polymer film and at least one metal film contacting the polymer film over its surface is provided. The polymer film comprises at least one fluid-permeable first opening and the metal film comprises at least one fluid-permeable second opening communicating with the first opening, wherein the metal film forms the heating elements, and wherein the heating elements are arranged so as to bound the second opening.

Furthermore, also known from WO 2016/166670 A1 is a film vaporizer comprising a flexible film having an electrically conductive network with resistance zones defining heating means. Furthermore, a flexible film is provided on which sections with aromatic substance are provided, which are arranged opposite the heating means, so that this substance can be volatilized. A very similar principle is also known from EP 3 282 872 61.

From EP 3 099 190 B1, a sine-shaped vaporizer film is known with a material surface piece designed for heating and absorbing a solution, and comprising a corrugation.

In solutions known in the prior art, the problem that liquid cannot be vaporized in a sufficient amount often arises. However, since the amount of vaporization depends essentially on the surface size of the vaporizer film, the increase in the amount of vaporization in the solutions known in the prior art is also inevitably accompanied by a larger space requirement. However, compactness in particular is an essential quality feature of electronic cigarette products or medical inhalers.

BRIEF SUMMARY OF THE INVENTION

It is the task of the invention to provide an improved vaporizer device for an inhaler, an improved inhaler and an improved cartridge. It is further the task of the invention to provide an improved method for operating and manufacturing a vaporizer device.

The invention solves the problem with the features of the independent claims. Further preferred embodiments of the invention can be found in the dependent claims, the figures and the accompanying description.

A medical inhaler in the meaning of the invention is a device suitable for making medicaments or homeopathic substances inhalable or for making them available for inhalation by a patient. Examples of substances vaporizable by such a medical inhaler include cannabinoids, for example cannabidiol or tetrahydrocannabinol, painkillers, or substances effective in connection with the treatment of asthma, COPD or other lung conditions or other diseases or medical conditions.

An electronic cigarette product in the meaning of the invention is a device suitable for making liquids or liquid mixtures, for example comprising polyglycol, glycerol and optionally nicotine and optionally aroma and/or flavoring agents inhalable or available for inhalation by a user.

According to the invention, it is proposed that the vaporizer film forms at least one supply channel via which the at least one first receiving opening can be supplied with liquid from the wick structure.

For the purposes of this application, a supply channel is understood to be a channel for conducting a liquid, wherein the liquid within the channel is conducted through at least two opposing surfaces of the channel.

The supply channel allows the first receiving opening of the vaporizer film to be spatially separated from the wick structure, so that the vaporizer film can be thermally decoupled from the wick structure and the liquid reservoir in the portions where the vaporizer film forms the at least one supply channel. The invention has recognized that in this way the energetic efficiency of the vaporizer device can be significantly improved because the energy introduced by the metal foil, which is formed as a heating element, can be used in a targeted manner to vaporize the liquid. Unwanted transfer of thermal energy via the wick structure to the liquid reservoir or to the liquid contained in the liquid reservoir can thus be reduced. As a result, a vaporizer device can be operated for a longer period of time without recharging, while maintaining the same battery capacity.

Furthermore, the at least one supply channel can increase the surface area of the vaporizer film that can be used for vaporization without increasing the base surface area, i.e., without requiring more space. Thus, the amount of vaporization per inhalation puff can be increased without the need for additional wicking materials.

It has been found advantageous to use a fleece, for example a glass fiber fleece, as the wick structure.

It has also proven advantageous to use the vaporizer film itself, which is present anyway, to form the supply channel. The vaporizer film is in contact with the wick structure via the base surface, so that the liquid to be delivered from the wick structure to the vaporizer film can be introduced into the supply channel in an efficient and reliable manner. For the purposes of this application, the base surface is the surface via which the vaporizer film is in contact with the wick structure.

The supply channel may be configured, for example, to supply fluid to a plurality of the first receiving openings of the vaporizer film.

A first receiving opening can, for example, be in fluidic communication with exactly one or more dispensing openings. Likewise, it is also possible, for example, for a plurality of first receiving openings to be in fluidic communication with precisely one or more dispensing openings.

By forming the at least one supply channel by means of the vaporizer film, the polymer film that is present anyway can be used to form the supply channel. Thus, the metal foil is also protected from the liquid in the supply channel when the at least one supply channel is formed.

Preferably, the vaporizer film is such that the metal film is completely embedded in the polymer film. The metal foil, which preferably comprises a meandering structure, is embedded in the polymer foil in such a way that sections with and without metal foil alternate within the polymer foil. The passage openings are then provided in the sections where no metal foil is embedded. This design of the vaporizer film can ensure that the liquid cannot come into contact with the metal film even during operation. It is thus possible to improve the system reliability characteristics, in particular the service life and reliability against failure, of the vaporizer device. Furthermore, it can be ruled out that the metal foil and the fluid react chemically to form a substance that is harmful to health.

In the embodiments shown below, any combination of two or more embodiments is also possible.

According to a further embodiment, the at least one supply channel is formed by a fold of the vaporizer film. By folding the vaporizer film, a supply channel can be produced with simple manufacturing measures. The vaporizer film can thus be manufactured at low cost.

Furthermore, it is advantageous if the fold comprises two opposing folding surfaces which are connected to one another via at least one folding edge, wherein at least 20%, preferably at least 30%, further preferably at least 50%, of the opposing folding surfaces are aligned parallel to one another. The at least partially parallel arrangement of the two folding surfaces can ensure suitable dimensioning of the supply channel. Furthermore, the capillary action can thereby be predefined in the best possible way.

For example, the extension of the fold, viewed along a direction orthogonal to an adjacent base surface of the vaporizer film, is at least 5 times the height of the vaporizer film, further for example 10 times, in particular for example 20 times. The spatial configuration of the vaporizer film achieved in this way creates an increased surface area that can be used for vaporizing the liquid, while the base surface remains the same. The height of the vaporizer film is preferably between 25 μm and 50 μm, further preferably between 30 μm and 40 μm.

The fold is preferably oriented such that it encloses an angle of between 30° and 150° with respect to the adjacent base surface of the vaporizer film or the upper side of the support element, further preferably between 80° and 100° and in particular an angle of 90°.

Since the first receiving openings are preferably provided at the folding surfaces, the fluid-permeable passage opening is flowed through in a direction parallel to the base surface when the fold is oriented orthogonally to the base surface.

It is further proposed that a plurality of the folds is provided, wherein the folds are spaced apart from each other by an intermediate portion of the vaporizer film. The plurality of folds can further enhance the positive effect associated with the supply channel or fold. The intermediate portion between two folds causes the folds to be spaced sufficiently far from each other so that the vaporized liquid can flow freely out of the dispensing openings provided at the folds. The vaporizer device can thus be designed to be more energetically efficient and the amount of vaporization can be increased. Preferably, the folding edges of the plurality of folds are arranged parallel to each other.

According to a further embodiment, at least one second receiving opening is provided, which is arranged at the base surface, wherein the at least one second receiving opening can be supplied with liquid directly via the wick structure. The second receiving opening is provided in addition to the at least one first receiving opening, so that the amount of vapor that can be generated can be increased. Preferably, a plurality of second receiving openings are provided on the base surface. By combining the at least one second receiving opening associated with the base surface and the at least one first receiving opening supplied with liquid via the at least one supply channel, the amount of vaporized liquid can be increased and, at the same time, the energetic efficiency of the vaporizer device can be increased. Preferably, the second receiving openings and the dispensing openings fluidically connected thereto are arranged on both sides with respect to the fold, so that vaporization of liquid can take place on both sides of the fold, both on the upper side of the vaporizer film and on the outer surfaces of the fold.

The aforementioned intermediate portion between two adjacent folds is particularly advantageous if the intermediate portion comprises at least one of the second receiving openings. The intermediate portion in fact preferably also comprises the base surface, so that between two folds it is additionally possible to dispense vaporized liquid via one or more dispensing openings which are supplied with liquid via one or more of the second receiving openings. The dispensing openings provided at the intermediate portion can further increase the amount of vaporization.

It is further proposed that at least 20%, for example at least 30%, further for example at least 50% of the areal extent of the vaporizer film serve to form the supply channel.

A areal extent of the vaporizer film within the meaning of this application is to be understood as the area which the vaporizer film can occupy as a maximum in the spread-out state, i.e. without the presence of folds, bends or other deformations. Typically, the vaporizer film is in such a maximally expanded state prior to installation in the vaporizer device.

The proposed ratio between the areal extent of the vaporizer film and the areal portion for forming the at least one supply channel can ensure that the technical effect associated with the supply channels, namely thermal insulation, is particularly advantageous and, at the same time, a sufficient amount of liquid to be vaporized can be supplied to the vaporizer film via the supply channels.

Usually, no contact with the wick structure is possible in the areas of the vaporizer film where it forms the supply channel. Therefore, it is further proposed that, for example, at least 10% of the areal extent of the vaporizer film forms the base surface, further for example at least 20%, in particular for example at least 30%. The abutment of the base surface against the wick structure is advantageous for efficiently guiding the liquid into the at least one supply channel, because the base surface merges directly into the supply channel. Furthermore, a corresponding minimum size of the base surface offers the advantage that—if present—the at least one second receiving opening, which may be provided at the base surface, can be sufficiently supplied with liquid.

According to a further embodiment, it is proposed that the at least one supply channel is configured to direct the fluid from the wick structure along a main flow direction to the at least one first receiving opening, wherein the main flow direction encloses an angle between 30° and 150°, in particular an angle between 80° and 100°, with the adjacent base surface. This orientation of the flow channel allows the at least one first receiving opening to be arranged in a different plane than the base surface. In addition to providing thermal decoupling, this also allows the geometry of the vaporizer film to be more flexible. Namely, the vaporizer film can comprise a spatial geometry that goes beyond the usual areal extent of film structures. In this way, the area usable for vaporizing liquid can be increased without having to increase the base surface.

If the base surface is configured as a planar plane, then the determination of the angle between the base surface and the main flow direction is self-evident. If the base surface is curved, the surface immediately adjacent to the supply channel is selected as the reference surface. Provided that several curved surfaces are adjacent to the supply channel, the angle between the main flow direction and a fictitious base surface determined by averaging the orientation of the adjacent base surfaces is used.

It is further proposed that an extension of the at least one supply channel in the orthogonal direction with respect to the adjacent base surface is at least 5 times, more preferably 10 times, the height of the vaporizer film. It has been shown that this extension of the supply channel in the orthogonal direction offers an ideal compromise between, on the one hand, sufficient thermal insulation and, on the other hand, sufficient supply of the least one first receiving opening with liquid to be vaporized. Thus, the overall energetic efficiency of the vaporizer device can be further improved.

The passage openings to be associated with the fold preferably comprise, in orthogonal direction with respect to the upper side of the vaporizer film which is opposite to the base surface, a distance from the upper side which corresponds to more than 50% of the extension of the fold in orthogonal direction with respect to the base surface, further preferably more than 60%, more preferably more than 70%. Thus, a sufficiently large liquid column is formed in the supply channel, which allows thermal decoupling of the metal foil designed as a heating element from the wick structure and the liquid reservoir.

It is further proposed that the at least one supply channel is dimensioned such that the liquid is transferred from the wick structure to the least one first receiving opening under the action of capillary forces. By utilizing the capillary forces, a more reliable supply of liquid to be vaporized can be provided to the at least one supply channel.

It is further proposed that a support element is provided, on the upper side of which the vaporizer film is arranged, and on the lower side of which the liquid reservoir is arranged, wherein an opening is provided for receiving the wick structure, wherein the opening fluidically connects the upper side to the lower side. Preferably, the vaporizer film, or a metal foil comprised therein, which is operable as a heating element, is attached to the upper side of the support element via a connecting means in the form of a soldered or sintered joint. For example, a plurality of liquid reservoirs, for example exactly two liquid reservoirs, can also be provided, which are connected to a common wick structure. The liquid reservoirs are preferably arranged on the lower side of the support element. Of course, each liquid reservoir can also be assigned its own wick structure. This ensures a homogeneous supply of liquid to the wick structure. For example, a single liquid reservoir can also be provided, which comprises a bar so that the wick structure is clamped between the liquid reservoir and the vaporizer film; this can improve the supply of liquid to the vaporizer film via the wick structure. The appropriate arrangement of the components with respect to the support element enables a stable structure that can withstand vibrations, wherein at the same time a reliable supply of liquid to be vaporized to the vaporizer film is enabled via the wick structure inserted into the opening.

According to another embodiment, it is proposed that the base surface is a flat surface. Alternatively, the base surface is the partial shell surface of a cylinder. By such a design of the base surface, which is indeed in contact with the wick structure, an advantageous wetting of the vaporizer film with liquid can take place, so that the at least one supply channel adjacent to the base surface can be sufficiently supplied with liquid.

When the base surface is configured in the form of a shell surface of a cylinder, it is advantageous when the wick structure comprises a cylindrical shape having a longitudinal axis, wherein the wick structure is surrounded by the base surface of the vaporizer film, wherein a main flow direction of the at least one supply channel extends in a radial direction with respect to the longitudinal axis of the wick structure. The surface of the vaporizer film opposite the wick structure thus corresponds to the geometry of the wick structure, such that the vaporizer film can be sufficiently wetted with liquid to be vaporized.

In the case of a wick structure having a basic cylindrical shape, it is further proposed that the vaporizer film is surrounded by an outer ring so that a flow channel is formed between the vaporizer film and the outer ring. The outer ring and the wick structure preferably comprise a common longitudinal axis. To form the flow channel, the outer ring then comprises an inner radius which corresponds at least to the maximum radial extent of the vaporizer film. Due to the flow channel formed in this way, the flow around the dispensing openings can be particularly advantageous, so that the vaporization quantity can be further increased.

The task mentioned at the beginning is also solved by an inhaler and a cartridge comprising a vaporizer device according to any one of claims 1 to 14.

Furthermore, the task mentioned at the beginning is solved by a method for operating a vaporizer device according to any one of claims 1 to 14, wherein an electrical heating voltage is applied to the vaporizer film to generate the liquid vapor.

Finally, the task mentioned at the beginning is solved by a method for manufacturing a vaporizer device, wherein the vaporizer device comprises a vaporizer film arranged on a support element, wherein the vaporizer film forms at least one supply channel, with which the vaporizer film can be supplied with liquid to be vaporized from a liquid reservoir via a wick structure, wherein the supply channel is formed by a fold of the vaporizer film, wherein the method comprises the following steps:

a) providing a base material for the manufacture of the vaporizer film comprising a substrate of polyimide having a copper lamination applied thereto on one side;
b) patterning the copper lamination by an etching process so that a copper pattern is formed on the substrate;
c) applying a polyimide cover layer to the side of the substrate with the copper pattern;
d) creating a passage opening through which an upper side of the vaporizer film is fluidically connectable to a lower side of the vaporizer film by means of a laser;

e) incising a folding edge by means of a laser so that an incision is formed;

f) folding the vaporizer film along the incised folding edge;

g) joining the folded vaporizer film to the support element.

By the proposed method, a vaporizer film having a fold can be easily manufactured, wherein the supply channel is formed by the fold. By the manufacturing method, on the one hand, a very thin vaporizer film can be produced, and on the other hand, a fold with a very narrow bending radius can also be realized by the incised folding edge. This can increase the surface area of the vaporizer film over which the vaporized liquid can be dispensed, so that overall the vaporization behavior can be improved by the manufacturing process. For example, Pyralux® HT or Pyralux® AP from DuPont can be used as the polyimide for the substrate. The layer thickness of the substrate is preferably between 5 and 50 μm, further for example between 20 and 30 μm and in particular preferably 25 μm. The layer thickness of the copper lamination is preferably between 1 and 10 μm, further preferably between 2 and 8 μm, more preferably 5 μm. The vaporizer film produced in this way offers the advantage that a supply channel is formed by the fold, via which the passage openings of the vaporizer film can then be supplied with liquid to be vaporized.

It is further proposed that in process step b) the following sub-steps are carried out:

b1) application of a photoresist to the copper lamination;

b2) exposure of the photoresist in predefined areas;

b3) developing the photoresist so that the remaining photoresist forms a protective layer for the copper lamination in the predefined areas;

b4) applying an etchant to the side with the developed photoresist so that the copper lamination remains on the substrate only in the predefined areas;

b5) removing of the remaining photoresist.

The photoresist, also called resist, can be laminated on, for example. Subsequent exposure can be carried out, for example, by means of direct illumination, in which only the predefined areas are specifically illuminated, or, for example, by means of mask exposure. In mask exposure, a mask is applied to the photoresist which is transparent in sections so that the areas to be exposed can be specifically illuminated by a light source. After developing the photoresist, only the predefined areas of the photoresist remain on the copper lamination, so that the copper lamination is protected at these points. By subsequently applying an etching substance to the side with the copper lamination and the developed photoresist, the copper is etched away in the areas where the developed photoresist does not exert its protective effect. The copper lamination thus remains on the substrate only at predefined areas, so that a copper pattern is formed on the substrate. In a subsequent step, the photoresist is removed again, known as stripping, so that only the substrate with the copper pattern remains. A copper pattern thus remains from the full-surface copper lamination.

Preferably, in process step c), a polyimide cover layer is applied by lamination in a vacuum press. The polyimide cover layer applied in this way prestresses the substrate with the copper pattern applied to it in such a way that the substrate comprises a concave bend on the side with the polyimide cover layer. The concave bend has proven to be advantageous because it enables a fold with a particularly tapered folding edge. To enable simple further processing despite the bend, the substrate with the copper pattern and polyimide cover layer is preferably fixed to a flat surface of a carrier in the prestressed state for further processing. Pyralux® HT0100 from DuPont, for example, can be used as the material for the polyimide cover layer.

It is further proposed that in process step e), contacting points for supplying the vaporizer film with an electrical heating voltage are additionally exposed by means of the laser. By exposing the contacting points is meant the removal of the polyimide cover layer at the corresponding points. In this way, a particularly cost-effective means is provided for supplying the vaporizer film with the appropriate heating voltage.

It is further proposed that in process step e) the vaporizer film is additionally cut to size for the connection to the support element. This makes it possible, for example, to produce a large-area layer system from which a plurality of vaporizer films can be cut out. In this way, the vaporizer film can be produced in large quantities in a cost-effective manner. By cutting to size, a vaporizer film can then be formed from the large-area layer system, the dimensions of which are such that it can be connected to a support element of the vaporizer device. This is preferably done in such a way that the supply channel formed by the fold directly contacts the wick structure, which is inserted in an opening of the support element.

BRIEF DESCRIPTION OF THE FIGURES

The invention will be explained below with reference to preferred embodiments with reference to the accompanying figures. Thereby shows FIG. 1 a schematic cross-sectional view of a vaporizer device with a supply channel.

DETAILED DESCRIPTION

Figure 1:
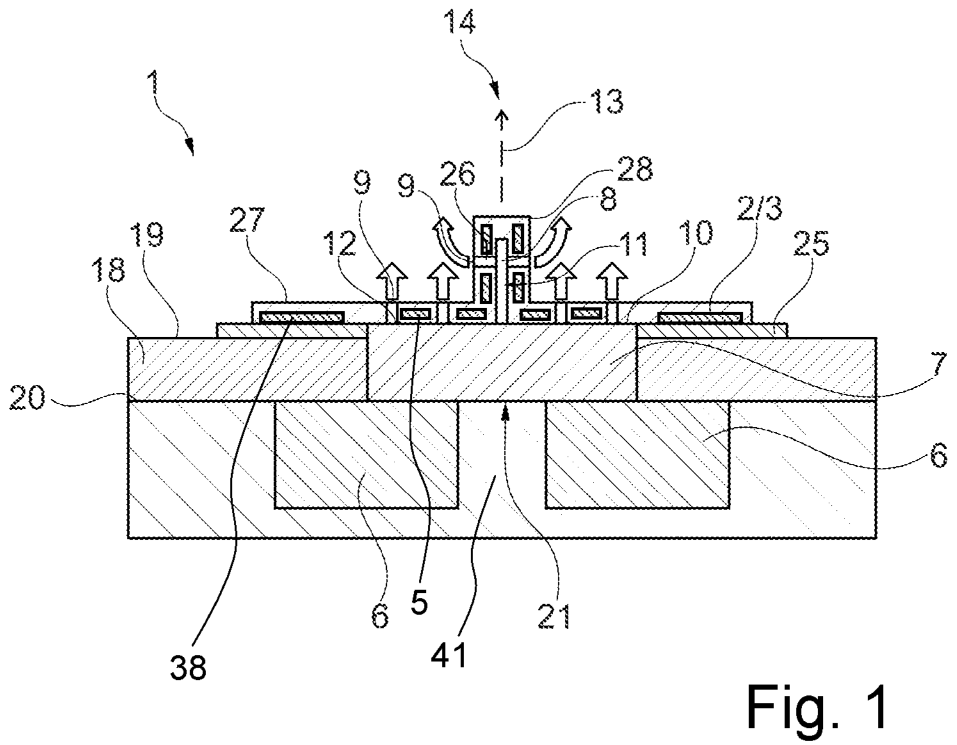

FIG. 1 shows a vaporizer device 1 comprising a vaporizer film 2, which is attached to an upper side 19 of a support element 18 via a connecting means 25, a liquid reservoir 6, which is arranged on a lower side 20 of the support element 18, and a wick structure 7, which is arranged to supply the vaporizer film 2 with liquid to be vaporized from the liquid reservoir 6.

Of course, it is in principle also possible to provide two or more liquid reservoirs 6.

The support element 18 comprises an opening 21 into which the wick structure 7 is inserted. Thus, the liquid to be vaporized can be conveyed from the liquid reservoir 6 by means of the wick structure 7 through the opening 21 to the vaporizer film 2. Furthermore, the liquid reservoir 6 comprises a bar 41 via which the wick structure 7 can be pressed in between the liquid reservoir 6 and the vaporizer film 2. In the embodiments shown, a fleece, for example a glass fiber fleece, is provided as the wick structure 7.

The vaporizer film 2, or a metal foil 5 included therein, which is operable as a heating element, is preferably connected to the support element 18 via a connecting means 25 in the form of a soldered or sintered connection.

Figure 2:
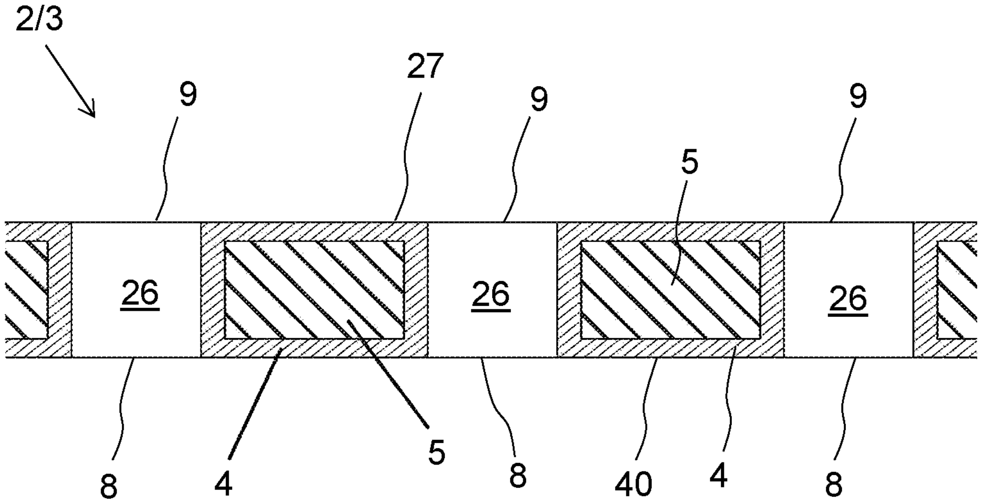
FIG. 2 a schematic cross-sectional view of a vaporizer film.

An exemplary illustration of the vaporizer film 2 is shown schematically in FIG. 2. The vaporizer film 2 comprises a layer system 3, which in turn comprises a polymer film 4 and the at least one metal foil 5 contacting the polymer film 4 on its surface. Preferably, the polymer film 4 is laminated onto the metal foil 5. In the embodiment according to FIG. 2, the metal foil 5 is completely surrounded by the polymer foil 4. The metal foil 5 is thus completely wrapped in the polymer foil 4. It can thus be ensured that the liquid cannot come into contact with the metal foil even during operation. The polymer film 4 is preferably a polyimide film.

The vaporizer film 2 is perforated so that a first receiving opening 8 on a lower side 40 can be fluidically connected to a dispensing opening 9 on an upper side 27. The first receiving opening 8 and the dispensing opening 9 thus together form a respective fluid-permeable passage opening 26.

The wick structure 7 shown in FIG. 1 is preferably made of a porous and/or capillary material which, due to capillary forces, is capable of passively replenishing liquid vaporized by the vaporizer film 2 from the liquid reservoir 6 to the vaporizer film 2 in sufficient quantity to prevent the passage opening 26 from running dry and any problems resulting therefrom.

The metal foil 5 according to FIG. 2 is arranged as a heating element, for example in the form of an ohmic heater. When the vaporizer film 2 of FIG. 2 is used as a component of the vaporizer device 1 of FIG. 1, vaporization of the liquid occurs within the passage opening 26, wherein the liquid is conveyed from the liquid reservoir 6 via the wick structure 7, for example, by capillary forces. In the operating state, activation of the metal foil 5 occurs in certain phases, for example when an inhalation puff is detected by a user, by application of a heating voltage to two contacting points 38 (see FIGS. 7 to 10) of the metal foil 5 and flow of an electric current through the metal foil 5 so that it heats up. Consequently, heat is also generated in the fluid-permeable passage opening 26. As the fluid flows through the fluid-permeable passage opening 26 starting from the first receiving opening 8, the fluid is heated to such an extent that it reaches the vaporous aggregate state and leaves the dispensing openings 9 as vapor. As a result of the vaporization, volume is freed up within the passage opening 26 into which liquid can creep due to the capillary forces. Further supply of liquid takes place via the supply channel 11 and the wick structure 7 from the liquid reservoir 6. During the vaporization process in the passage opening 26, there is thus a continuous replenishment of liquid from the liquid reservoir 6 via the wick structure 7.

As can be seen from FIG. 1, the first two receiving openings 8 are not directly supplied with liquid via the wick structure 7. The supply takes place via a supply channel 11 fluidically connected between the first receiving opening 8 and the wick structure 7, which is formed by the vaporizer film 2 itself.

Figure 5:
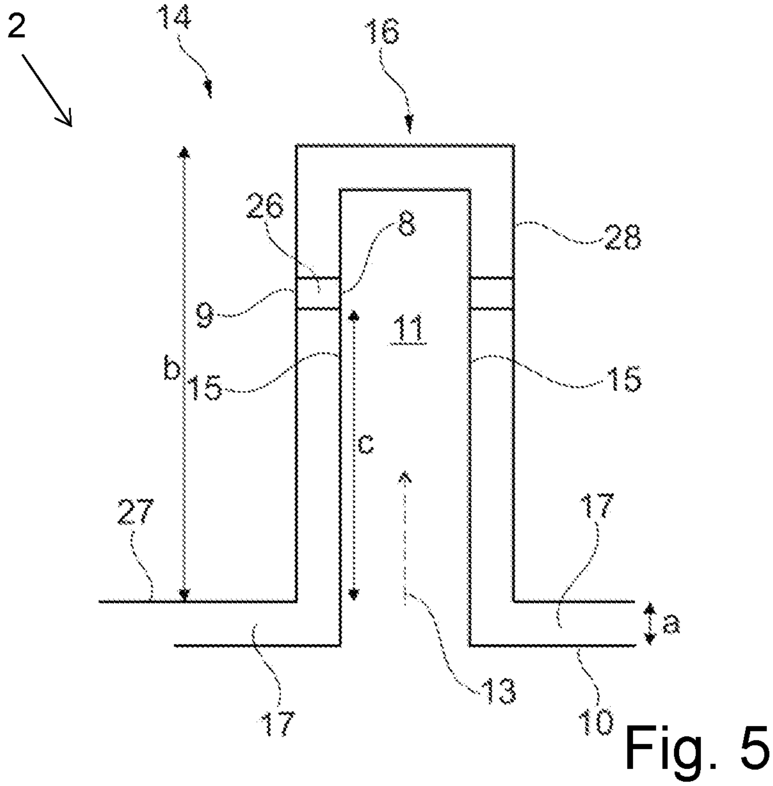
FIG. 5 a schematic cross-sectional view of a fold of a vaporizer film.

The supply channel 11 is formed by a fold 14 of the vaporizer film 2, which is shown enlarged in a cross-sectional view in FIG. 5. The fold 14 of the vaporizer film 2 forms two opposing folding surfaces 15, which are connected to each other by a folding edge 16. The opposing folding surfaces 15 of a fold 14 can be irregularly shaped, but are aligned parallel to one another, for example, in partial sections or partial surfaces whose proportion of the total area of the folding surfaces 15 is, for example, more than 20%. A parallel extension of the opposing folding surfaces 15 is advantageous, because in this way the effect of the capillary forces can be predefined in the best possible way.

Preferably, the extension b of the fold 14 in a direction orthogonal to an adjacent base surface 10 of the vaporizer film 2 is at least 5 times the height a of the vaporizer film 2. This results in a more spatially pronounced design of the vaporizer film 2 in comparison to the otherwise only planar arranged vaporizer films 2 from the prior art.

The fold 14 is designed in such a way that it is oriented perpendicularly with respect to the base surface 10 or to an upper side 19 of the support element 18, comp. FIG. 1. By a perpendicular orientation of the fold 14 is meant that its folding surfaces 15 are oriented orthogonally to the adjacent base surface 10.

Thus, the supply channel 11 formed by the fold 14 is also oriented perpendicularly with respect to the base surface 10. This configuration of the fold 14 results in a main flow direction 13 of the fluid within the supply channel 11. The main flow direction 13 is the flow direction in which the majority of the fluid flows from the wick structure 7 to a first receiving opening 8 within the at least one supply channel 11. Accordingly, the main flow direction 13 is also oriented orthogonally with respect to the base surface 10 adjacent to the fold 14.

The two first receiving openings 8 are provided at the folding surfaces 15, so that the fluid-permeable passage openings 26 are flowed through in a direction which is oriented parallel to the base surface 10.

Further, the fold 14 in FIG. 5 comprises exactly two of the fluid-permeable passage openings 26. Of course, the fold 14 may comprise only a single one of the passage openings 26, or more than two of the passage openings 26. Where multiple passage openings 26 are provided, they may also be arranged in series with respect to an axis perpendicular to the drawing plane of FIG. 5. Alternatively or additionally, the passage openings 26 may also be arranged one above the other with respect to an axis orthogonal to the base surface 10.

The passage openings 26 shown in FIG. 5 comprise in the orthogonal direction with respect to the upper side 27 of the vaporizer film 2 which is opposite to the base surface 10, a distance c from the upper side 27 which corresponds to more than 50% of the extension b in the orthogonal direction of the fold 14, preferably more than 60%, further preferably more than 70%. This spacing of the passage openings 26 and thus also of the first receiving openings 14 from the upper side 27 can ensure a sufficient liquid column in the supply channel 11, so that thermal decoupling of the metal foil 5 designed as a heating element is made possible. The column of liquid located in the fold 14 causes the metal foil 5, which gives off thermal energy during operation, to be insulated from the wick structure 7 and the two liquid reservoirs 6, so that the energy efficiency of the vaporizer device 1 can be increased.

When the vaporizer device 1 of FIG. 1 is operated, the heat generated in the fluid-permeable passage opening 26 causes the liquid to be vaporized to be fed from the liquid reservoirs 6 into the passage opening 26 by means of the wick structure 7 and the supply channel 11. There, the liquid is heated at least to boiling temperature so that the fluid vaporizes and escapes from the dispensing opening 9 in a gaseous state. During this process, i.e. while the metal foil 5 is activated, i.e. heats, fluid is continuously supplied from the liquid reservoirs 6 by means of the wick structure 7 and the supply channel 11 or through it, so that continuous vaporization of fluid can take place.

Furthermore, it can be seen from FIG. 1 that the dispensing of the vapor does not only take place via the dispensing openings 9, which are associated with an outer surface 28 perpendicular to the base surface 10 of the fold 14. In addition, dispensing openings 9 are also arranged on the vaporizer film 2 on the upper side 27 of the vaporizer film 2, which is opposite the base surface 10. These dispensing openings 9 are fluidically connected to second receiving openings 12, which can be supplied with liquid directly via the wick structure 7. The second receiving openings 12 are thus not supplied with liquid via the supply channel 11. The passage openings 26 associated with the second receiving openings 12 can, however, be designed in exactly the same way as those which are supplied with liquid via the supply channel 11; in this respect, reference is made to the explanations on FIG. 2.

The combination of first receiving openings 8, which are supplied via the supply channel 11, and second receiving openings 12, which are supplied directly via the wick structure 7, allows vaporized liquid to be dispensed in different spatial directions, so that overall the surface area of the vaporizer film 2 that can be used for vaporization via the dispensing openings 9 is increased. Thus, the total amount of vaporization per inhalation puff can be increased.

Figure 3:
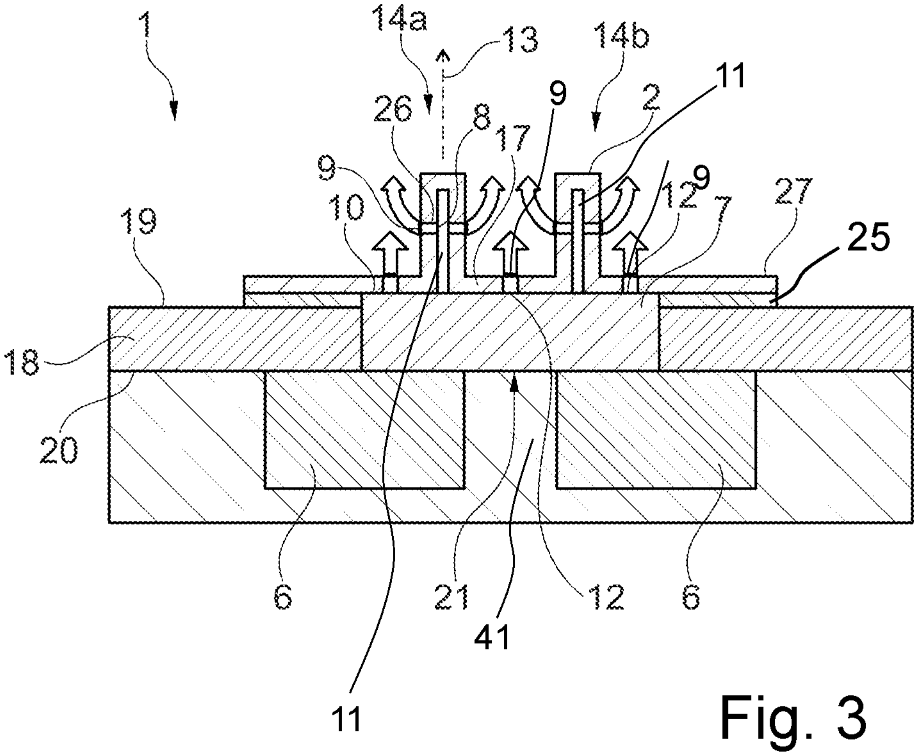
FIG. 3 a schematic cross-sectional view of a vaporizer device with two supply channels.

FIG. 3 shows a vaporizer device 1 with the same basic structure as the vaporizer device 1 of FIG. 1, but with the difference that in addition to the first fold 14*a*, a second fold 14*b* is provided, which is spaced from the first fold 14*a* by an intermediate portion 17.

Each of the two folds 14*a* and 14*b* comprises two first receiving openings 8 and dispensing openings 9 associated therewith. Of course, the number of receiving openings 8 and the number of passage openings 26 correlating therewith can be varied as desired, as has already been explained in the embodiment according to FIG. 1.

Furthermore, the intermediate portion 17 also comprises at least one second receiving opening 12, which is supplied with liquid directly via the wick structure 7. In addition, a further second receiving opening 12 is provided to the left of the first fold 14*a* and to the right of the second fold 14*b*, respectively. This arrangement has proved to be advantageous because vaporized liquid can flow around each of the folds 14*a* and 14*b* on both sides starting from the second receiving openings 12, and at the same time an additional flow around the folds 14*a* and 14*b* is made possible starting from the first receiving openings 8 which are associated with the folds 14*a* and 14*b* directly. In this way, the amount of vaporization per inhalation puff can be significantly increased and, at the same time, the thermal decoupling of the metal foil 5 with respect to the wick structure 7 or the two liquid reservoirs 6 can be increased due to the insulating effect of the liquid column present in the supply channels 11 of the first and second folds 14*a* and 14*b*.

Of course, more than two folds 14*a* and 14*b* may be provided, further increasing the effect. Where multiple folds 14*a* and 14*b* are provided, they are preferably aligned parallel to each other, i.e. the folding edges 16 of the multiple folds 14*a* and 14*b* are aligned parallel to each other. Furthermore, for example, all main flow directions 13 in the supply channels 11 formed by the folds 14 are oriented orthogonally to the base surfaces 10 adjacent to the respective fold 14.

Figure 4:
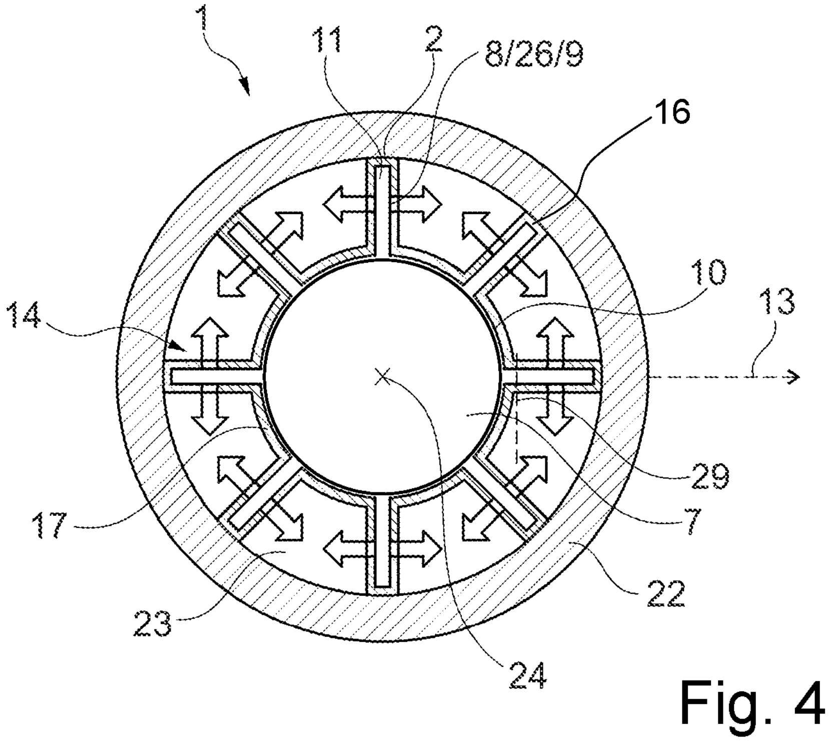
FIG. 4 a sectional cross-sectional view of a vaporizer device with a cylindrical wick structure.

FIG. 4 shows an embodiment of the vaporizer device 1 having a cylindrical wick structure 7 with a longitudinal axis 24 of the wick structure 7 oriented perpendicular to the drawing plane. It can be seen that the vaporizer film 2 surrounds the circumferential surface of the cylindrical wick structure 7, wherein a plurality of folds 14 are provided extending in a radial direction with respect to the longitudinal axis 24. This means that the folding edge 16, comp. also FIG. 5, is furthest away from the longitudinal axis 24 in the radial direction with respect to the longitudinal axis 24. The folding edge 16 is then aligned parallel to the longitudinal axis 24, for example.

In the embodiment according to FIG. 4, the supply channels 11 are formed by a plurality of folds 14. In this embodiment, vaporization of the liquid takes place exclusively via passage openings 26, which are supplied with liquid via first receiving openings 8 through a supply channel 11.

Of course, in addition to the passage openings 26 associated with the folds 14, passage openings 26 can also be provided which are supplied with liquid directly via the wick structure 7, i.e. via a second receiving opening 12. For example, at least one passage opening 26 can be provided between each fold 14, which is supplied with liquid via a second receiving opening 12.

In the case of a cylindrical wick structure 7, the base surface 10 is not flat but a curved surface. In this case, if the main flow direction 13 in the supply channel 2 is oriented orthogonally to the adjacent base surface 10, then in the cross-sectional view shown in FIG. 4, this refers to a tangent 29 through the point of the base surface 10 immediately adjacent to the fold 14.

The corresponding liquid reservoir 6, which supplies liquid to the wick structure 7, is not shown in FIG. 4. However, this may be arranged, for example, behind and/or in front of the wick structure 7 in the axial direction with respect to the longitudinal axis 24. Accordingly, the liquid to be vaporized is transported out of the liquid reservoir 6 in the axial direction by the wick structure 7 and then deflected in the radial direction with respect to the longitudinal axis 24 in order to deliver the liquid to be vaporized to the vaporizer film 2 or to the supply channel 11 formed by the vaporizer film 2.

In the embodiment according to FIG. 4, the vaporizer film 2 is surrounded by an outer ring 22, so that a plurality of flow channels 23 is formed between the vaporizer film 2 and the outer ring 22. During an inhalation puff by a user, flow then passes through the plurality of flow channels 23 in the direction of the longitudinal axis 24.

Figure 6:
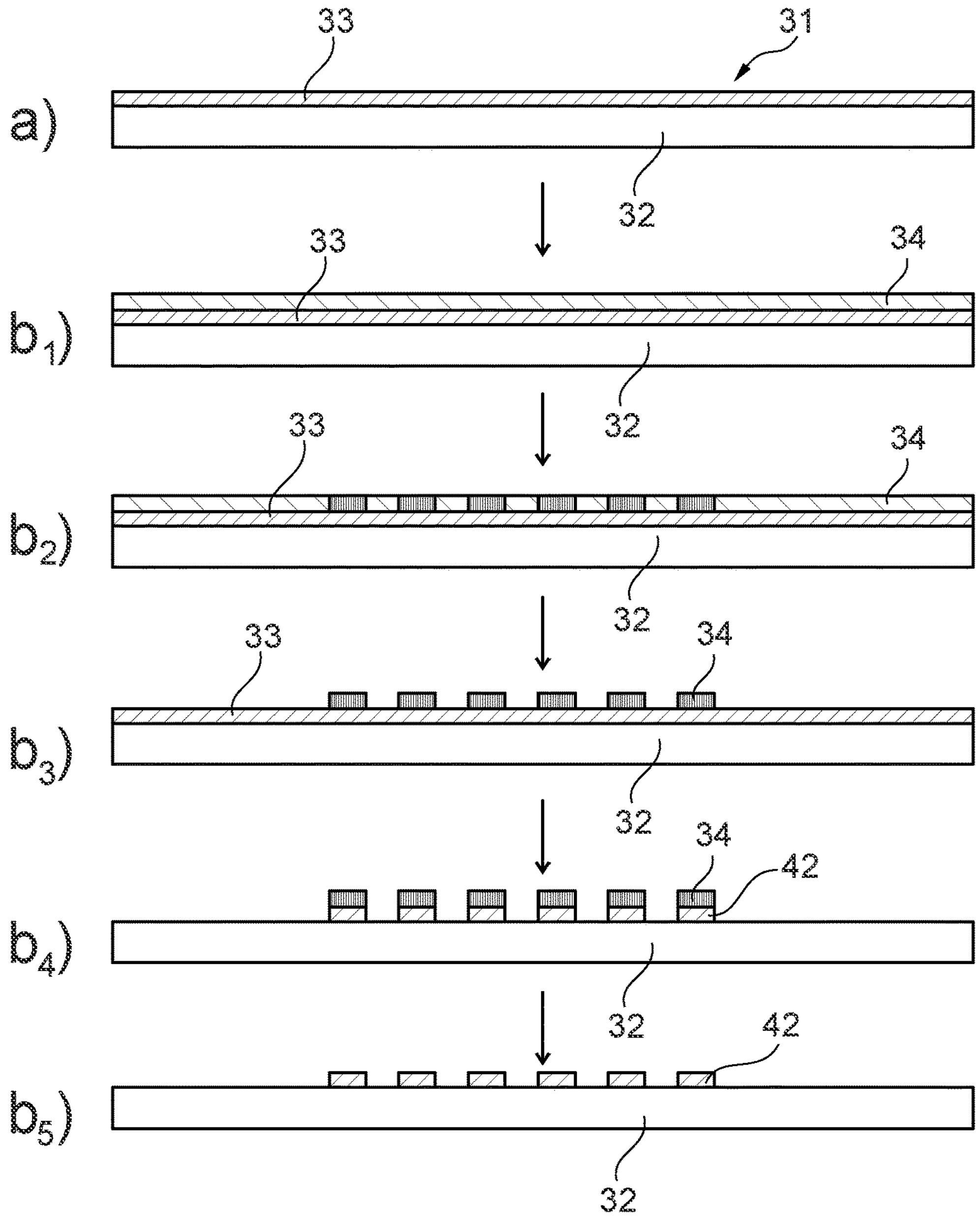
FIG. 6 the steps a) and b) of a manufacturing process of a vaporizer device.
Figure 6:
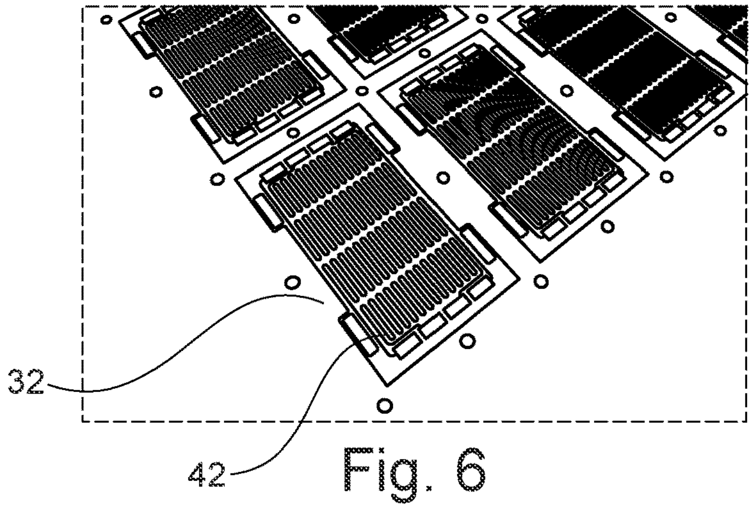

FIG. 6 shows the method steps a) and b) of a method 30 for manufacturing the vaporizer device 1. In a first method step a), a base material 31 comprising a substrate 32 and a copper lamination 33 applied thereto is provided.

The subsequent process step b), in which the copper lamination 34 is patterned to produce a copper pattern 42, is subdivided into process steps b1) to b5). In process step b1), a photoresist 34 is laminated onto the copper lamination 33, which is exposed in predefined areas in process step b2). This can be done, for example, by appropriate direct illumination or by means of a mask. In process step b3), the photoresist 34 is developed, i.e. only a resist mask resulting from the exposure remains on the copper lamination 33; the remaining photoresist 34 is removed. In process step b4), an etchant is applied to the side with the developed photoresist 34 so that the copper lamination is etched away at the areas where there is no protection by the resist mask formed by the photoresist 34. A copper pattern 42 is thus formed from the copper lamination 33 covering the entire surface. In process step b5), the remaining photoresist 34 is then removed so that only the copper pattern 42 remains on the substrate 32. Preferably, the copper pattern 42 comprises a meander shape. The result of process step b), namely the copper pattern 42 deposited on the substrate 32, is shown schematically in FIG. 6 below.

Figure 7:
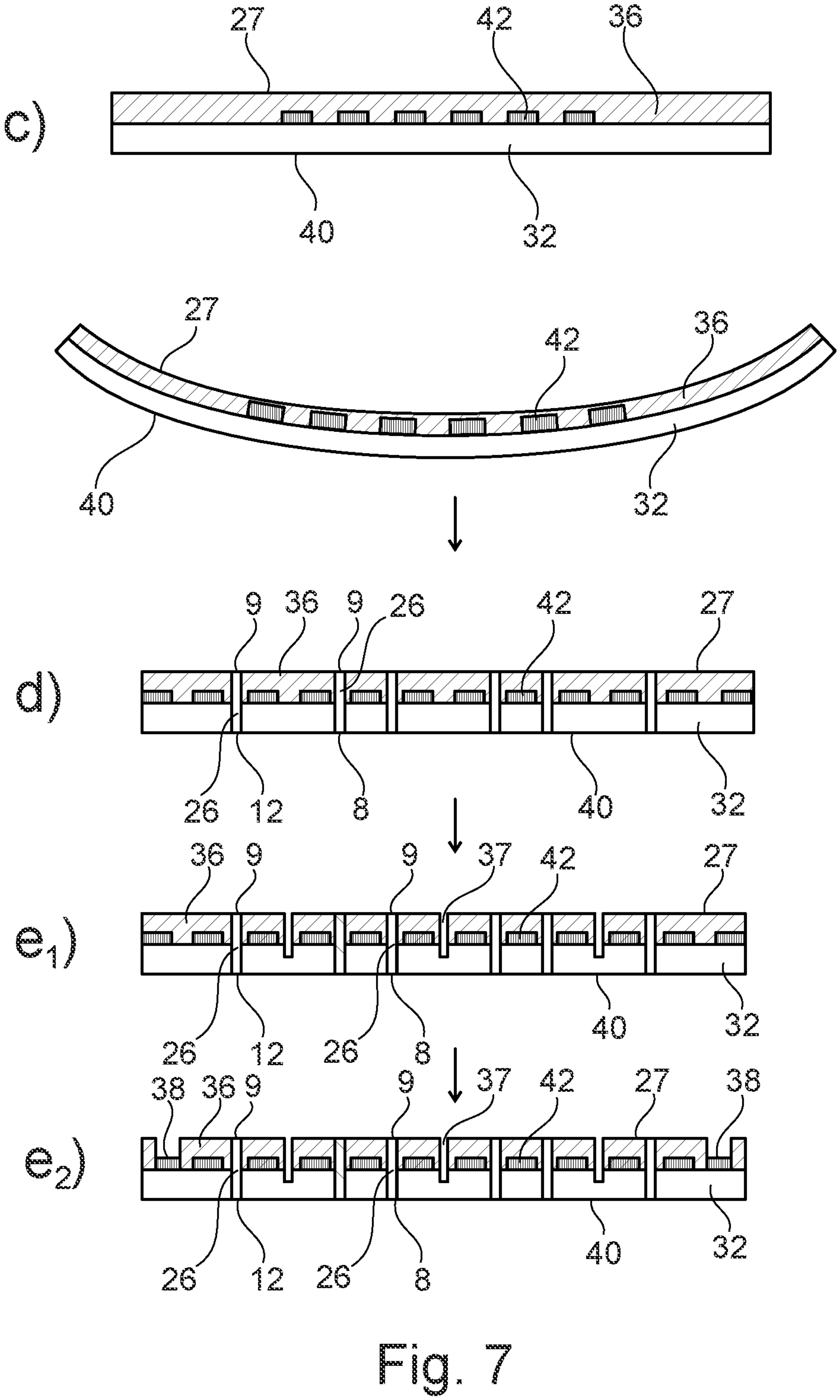
FIG. 7 the steps c) to e) of a manufacturing process of a vaporizer device.

FIG. 7 shows the process steps c) to e) of process 30. In process step c), a polyimide cover layer 36 is applied to the side of the substrate 32 with the copper pattern 42, so that the copper pattern 42 forming the metal foil 5 (see FIG. 2) is completely embedded in layers of polyimide, i.e. the substrate 32 formed from polyimide and the polyimide cover layer 36. The polyimide cover layer 36 is laminated on one side in a vacuum press, which results in a curvature of the intermediate product thus formed and in such a way that the upper side 27, i.e. the side with the polyimide cover layer 36, is concavely curved; see illustration in FIG. 7 c) below.

In process step d), the intermediate product now present, comprising the substrate 32, the copper pattern 42 and the polyimide cover layer 36, is then perforated by means of a laser, so that fluidic connections are formed between the upper side 27 and the lower side 12. In this way, the passage openings 26 are formed, which connect the first and second receiving openings 8 and 12 respectively with the dispensing openings 9; see also FIGS. 1 to 5. As can be clearly seen in FIG. 7, the perforation is carried out exclusively in areas in which no copper pattern 42 is located, i.e. between two areas with a copper pattern 42.

In process step e1), a folding edge 16 is then additionally incised by means of a laser, wherein a resulting incision 37 preferably completely penetrates the polyimide cover layer 36, the substrate 32 is preferably only partially incised. In process step e2), several contacting points 38 are exposed by means of the laser, i.e. the polyimide cover layer 36 is removed by the laser at the corresponding point until part of the copper pattern 42 is exposed.

If necessary, the vaporizer film 2 can still be cut or trimmed as an intermediate step so that it comprises the correct size for connecting to the support element 18.

Figure 8:
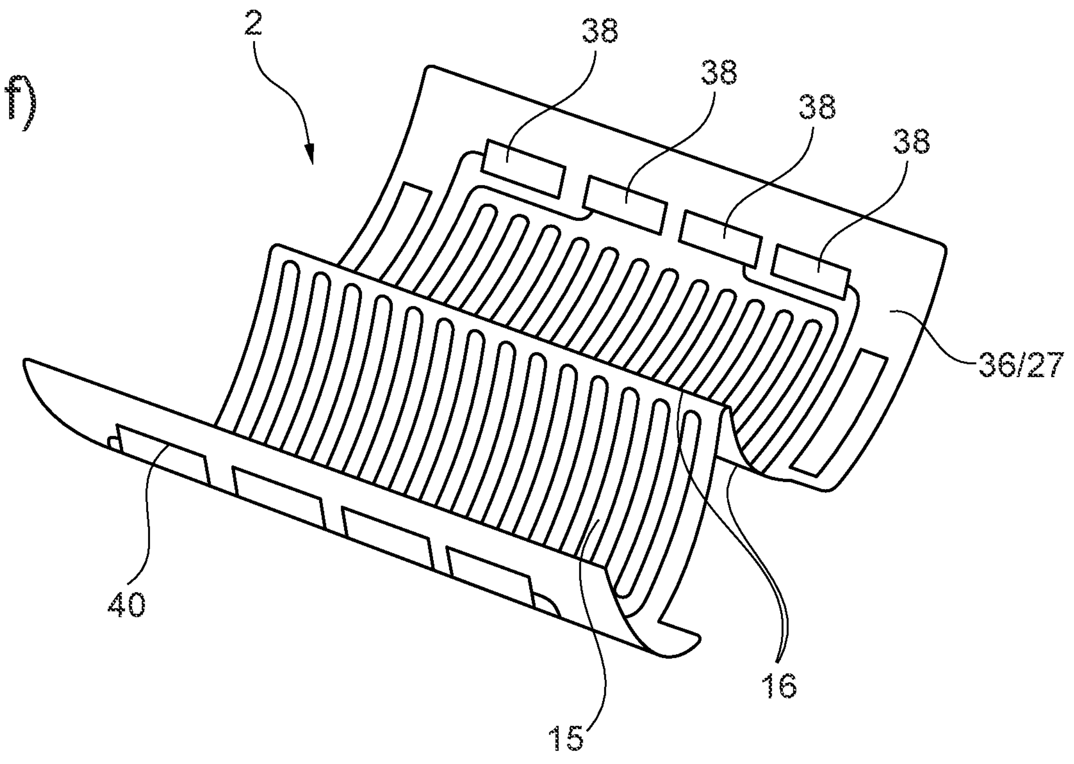
FIG. 8 a vaporizer film after performing the process step f) from a first perspective.
Figure 9:
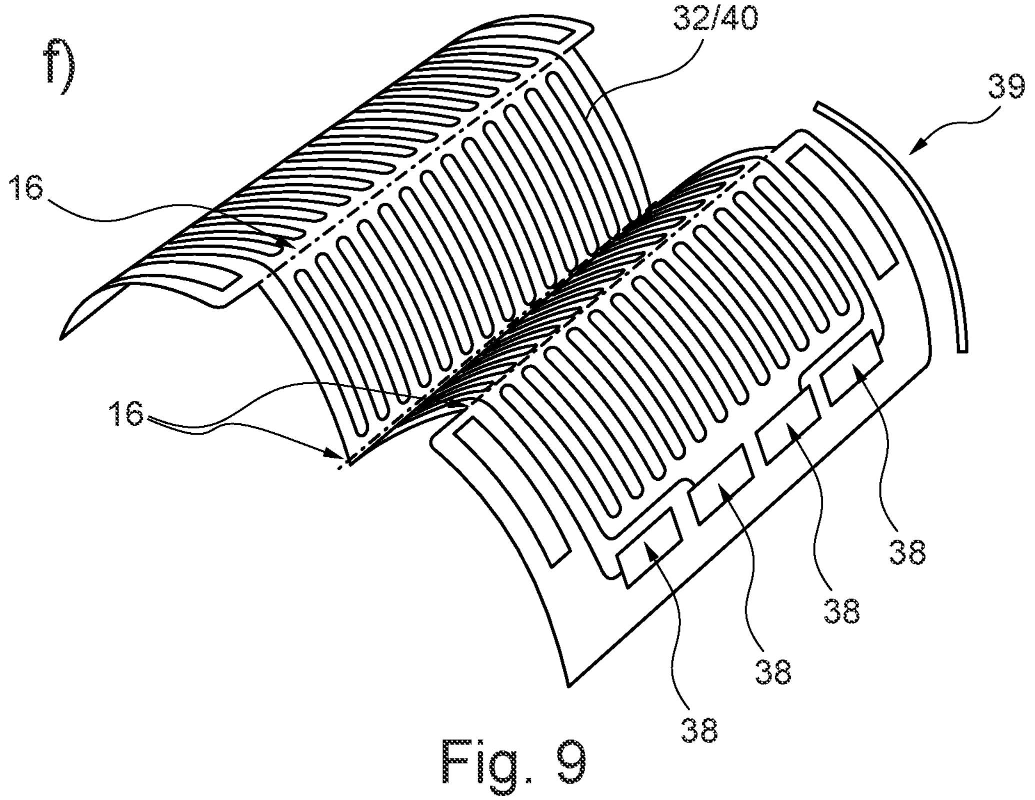
FIG. 9 a vaporizer film after performing process step f) from a second perspective.

FIGS. 8 and 9 show the vaporizer film 2 in a folded state, and thus the result of process step f). The folding is performed along the incised folding edges 16, so that sharp folding edges 16 can be obtained. FIG. 8 shows the vaporizer film 2 from a perspective looking at the upper side 27. It can be clearly seen that the folding surfaces 15 are curved due to the pre-stressing generated in process step c). Furthermore, the contact points 38 as well as the meander-shaped copper pattern 42 shimmering through the polyimide cover layer 36 can be seen.

FIG. 9 shows the vaporizer film 2 from a perspective looking at the lower side 40. Furthermore, a curvature 39 of the vaporizer film 2 is indicated.

Figure 10:
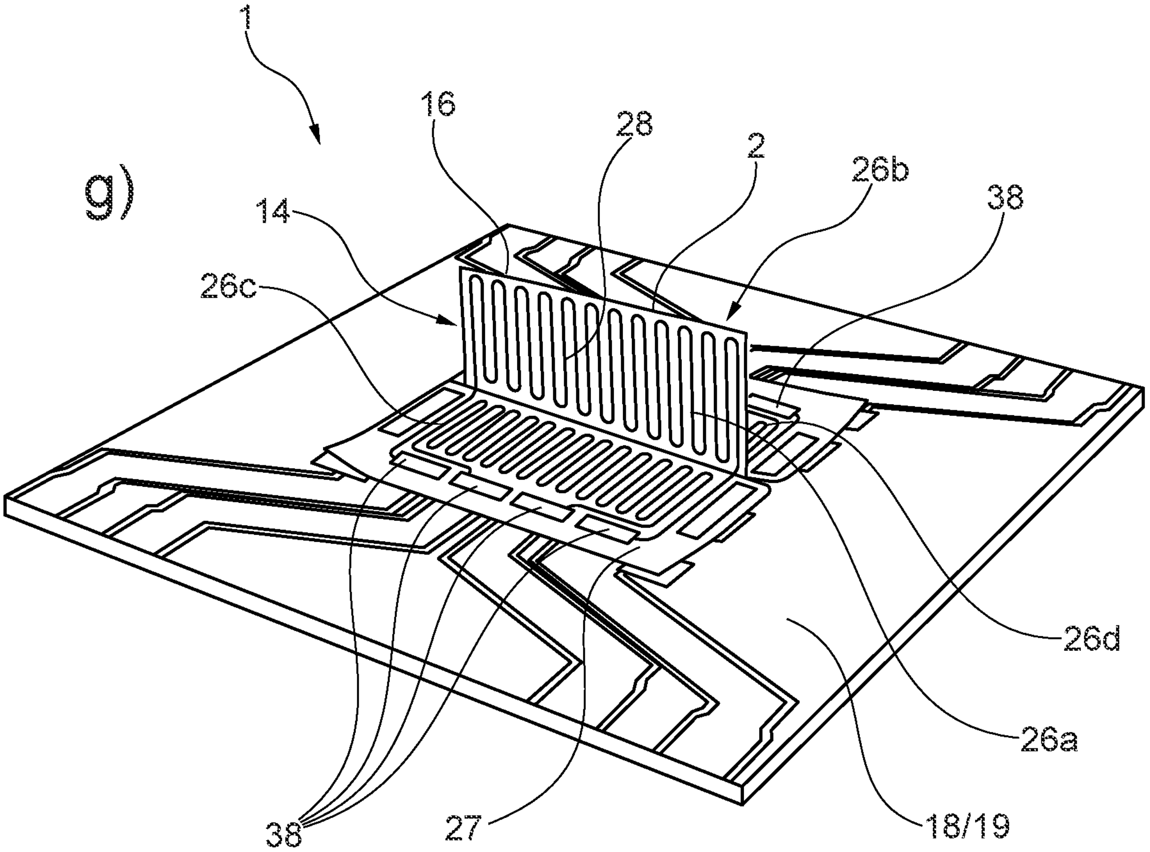
FIG. 10 a vaporizer device after carrying out process step g) from a perspective view.

FIG. 10 shows the vaporizer film 2 in a state connected to the support element 18, i.e. after completion of process step g).

FIG. 10 shows a perspective view of a vaporizer device 1 with a similar basic structure as the embodiment of the vaporizer device 1 shown in FIG. 1. It can be seen that the fold 14 protrudes like a fin from the plane formed by the upper side 27 of the vaporizer film 2.

Due to the curvature 39 of the vaporizer film 2 generated in the process step c), the fold 14 in the state connected to the support element 18 comprises a prestress, which results in the fold 14 comprising a more stable structure and the sharp folding edge 16 can also be maintained permanently, as for example in operation, in transport situations or in case of improper handling. It can further be seen that the vaporizer film 2 is connected to the upper side 19 of the support element 18. The vaporizer film 2 comprises four passage openings 26*a*, 26*b* (not visible rear side of the fold 14), 26*c* and 26*d*, wherein two passage openings 26*a* and 26*b* are each supplied with liquid to be vaporized through a first receiving opening 8 (comp. FIG. 1) and two further passage openings 26*c* and 26*d* are each supplied with liquid to be vaporized through a second receiving opening 12 (comp. FIG. 1). Accordingly, a discharge of the vaporized liquid takes place on both sides of the fold 14 both on an upper side 27 of the vaporizer film 2 and simultaneously on the outer surfaces 28 of the fold 14.

As described above, the metal foil 5 formed by the copper pattern 42 comprises meander-shaped patterns within the polymer foil 4 formed by the substrate 32 and the polyimide cover layer 36, wherein the meander-shaped patterns comprise separately controllable sections. Separately controllable means that the respective section comprises separate contacting points 38 and thus the heating voltage applied to the respective section is individually adjustable. For this purpose, the respective section is electrically insulated from the other sections of the copper pattern 42. A separately controllable section of the copper pattern 42 is referred to as a controllable channel. Each of these sections forms an ohmic heater, wherein it has been found advantageous if each separately drivable section of the metal foil 5 or metal pattern 42 comprises a resistance between 1 and 3Ω, for example about 2Ω. Preferably, the embodiment in FIG. 10 comprises four separately controllable channels, wherein the passage openings 26*a*, 26*b*, 26*c* and 26*d* are each associated with one of these four channels, so that the passage openings 26*a* to 26*d* are separately controllable via the channels.

By attaching the vaporizer film 2 to the support element 18 and/or to the wick structure 7 by means of the connecting means 25, the vaporizer film 2 can be reliably held in the transformed position.

With the vaporizer device 1 according to FIG. 10, it is possible, for example, to vaporize an amount of 7.4 mg of liquid during an inhalation puff of three seconds; at the same time, an energetic efficiency of 60% and more can be achieved under usual room conditions.

EMBODIMENTS

Embodiment 1. Vaporizer device (1) for an inhaler, in particular for an electronic cigarette product or a medical inhaler, comprising a vaporizer film (2), which in turn comprises a layer system (3) with a polymer film (4) and at least one metal foil (5), which makes surface contact with the polymer film (4) and is designed as a heating element, a liquid reservoir (6), and a wick structure (7), which is arranged to supply the vaporizer film (2) with liquid from the liquid reservoir (6), wherein the vaporizer film (2) comprises at least one first receiving opening (8) for receiving liquid and at least one dispensing opening (9) for dispensing vaporized liquid, wherein the vaporizer film (2) is in contact with the wick structure (7) via the base surface (10), characterized in that the vaporizer film (2) forms at least one supply channel (11), via which the at least one first receiving opening (8) can be supplied with liquid from the wick structure (7).

Embodiment 2. Vaporizer device (1) according to embodiment 1, characterized in that the at least one supply channel (11) is formed by a fold (14) of the vaporizer film (2).

Embodiment 3. Vaporizer device (1) according to embodiment 2, characterized in that the fold (14) comprises two opposing folding surfaces (15) which are connected to one another via at least one folding edge (16), wherein at least 20% of the opposing folding surfaces (15) are aligned parallel to each other.

Embodiment 4. Vaporizer device (1) according to any one of embodiments 2 or 3, characterized in that a plurality of said folds (14) are provided, wherein the folds (14) are spaced apart by an intermediate portion (17) of said vaporizer film (2).

Embodiment 5. Vaporizer device (1) according to any one of the preceding embodiments, characterized in that at least one second receiving opening (12) is provided, which is arranged on the base surface (10), wherein the at least one second receiving opening (12) can be supplied with liquid directly via the wick structure (7).

Embodiment 6. Vaporizer device (1) according to any one of the preceding embodiments, characterized in that at least 20% of the areal extent of the vaporizer film (2) forms the at least one supply channel (11).

Embodiment 7. Vaporizer device (1) according to any one of the preceding embodiments, characterized in that the at least one supply channel (11) is configured to direct the liquid from the wick structure (7) along a main flow direction (13) to the at least one first receiving opening (8), wherein the main flow direction (13) encloses an angle between 30° and 150°, in particular an angle between 80° and 100°, with the adjacent base surface (10).

Embodiment 8. Vaporizer device (1) according to any one of the preceding embodiments, characterized in that an extension (b) of the at least one supply channel (11) in orthogonal direction with respect to the adjacent base surface (10) corresponds to at least 5 times the height (a) of the vaporizer film (2).

Embodiment 9. Vaporizer device (1) according to any one of the preceding embodiments, characterized in that the at least one supply channel (11) is dimensioned such that the liquid is transferred from the wick structure (7) to the at least one first receiving opening (8) under the action of capillary forces.

Embodiment 10. Vaporizer device (1) according to any one of the preceding embodiments, characterized in that a support element (18) is provided, on the upper side (19) of which the vaporizer film (2) is arranged, and on the lower side (20) of which the liquid reservoir (6) is arranged, wherein an opening (21) is provided for receiving the wick structure (7), wherein the opening (21) fluidically connects the upper side (19) to the lower side (20).

Embodiment 11. Vaporizer device (1) according to any one of the preceding embodiments, characterized in that the base surface (10) is a flat surface.

Embodiment 12. Vaporizer device (10) according to any one of embodiments 1 to 10, characterized in that the base surface (10) is the partial shell surface of a cylinder.

Embodiment 13. Vaporizer device (1) according to embodiment 12, characterized in that the wick structure (7) comprises a cylindrical shape with a longitudinal axis (24), wherein the wick structure (7) is surrounded by the base surface (10) of the vaporizer film (2), wherein a main flow direction (13) of the at least one supply channel (11) extends in a radial direction with respect to the longitudinal axis (24) of the wick structure (7).

Embodiment 14. Vaporizer device (1) according to embodiment 13, characterized in that the vaporizer film (2) is surrounded by an outer ring (22) so that a flow channel (23) is formed between the vaporizer film (2) and the outer ring (22).

Embodiment 15. Inhaler comprising a vaporizer device (1) according to any one of the preceding embodiments.

Embodiment 16. Cartridge for an inhaler comprising a vaporizer device (1) according to any one of embodiments 1 to 14.

Embodiment 17. Method for operating a vaporizer device (1) according to any one of embodiments 1 to 14, wherein an electrical heating voltage is applied to the vaporizer film (1) to generate the liquid vapor.

Embodiment 18. Method (30) for manufacturing a vaporizer device (1), wherein the vaporizer device (1) comprises a vaporizer film (2) arranged on a support element (18), wherein the vaporizer film (2) forms at least one supply channel (11), with which the vaporizer film (2) can be supplied via a wick structure (7) with liquid to be vaporized from a liquid reservoir (6), wherein the supply channel (11) is formed by a fold (14) of the vaporizer film (2), wherein the method (30) comprises the following steps:

a) providing a base material (31) for the manufacture of the vaporizer film (2) comprising a substrate (32) of polyimide with a copper lamination (33) applied thereto on one side;

b) patterning the copper lamination (33) by an etching process so that a copper pattern (42) is formed on the substrate (32); c) applying a polyimide cover layer (36) to the side of the substrate (32) with the copper pattern (42);

d) creating a passage opening (26) through which an upper side (27) of the vaporizer film (2) is fluidically connectable to a lower side (40) of the vaporizer film (2) by means of a laser;

e) incising a folding edge (16) by means of a laser so that an incision (37) is formed;

f) folding the vaporizer film (2) along the incised folding edge (16);

g) joining the folded vaporizer film (2) to the support element (18).

Embodiment 19. Process (30) according to embodiment 18, characterized in that in process step b) the following sub-steps are carried out:

b1) applying a photoresist (34) to the copper lamination (33);

b2) exposure of the photoresist (34) in predefined areas;

b3) developing the photoresist (34) so that the remaining photoresist (34) forms a protective layer for the copper lamination (33) in the predefined areas;

b4) applying an etchant to the side with the developed photoresist (34) so that the copper lamination (33) remains on the substrate (32) only in the predefined areas;

b5) removing the remaining photoresist (34).

Embodiment 20. Process (30) according to embodiment 18 or 19, characterized in that in process step c) the application of a polyimide cover layer (36) is carried out by lamination in a vacuum press.

Embodiment 21. Process (30) according to any one of embodiments 18 to 20, characterized in that in process step e) contacting points (38) for supplying the vaporizer film (2) with an electrical heating voltage are additionally exposed by means of the laser.

Embodiment 22. Process (30) according to any one of embodiments 18 to 21, characterized in that in process step e) the vaporizer film (2) is additionally cut to size for connection to the support element (18).

The invention claimed is:

1. A vaporizer device for an inhaler, comprising:

a vaporizer film, wherein the vaporizer film comprises a layer system with a polymer film and at least one metal foil, wherein the at least one metal foil makes surface contact with the polymer film and is designed as a heating element, a liquid reservoir, and a wick structure, which is arranged to supply the vaporizer film with liquid from the liquid reservoir, wherein the vaporizer film comprises at least one first receiving opening for receiving the liquid and at least one dispensing opening for dispensing vaporized liquid, wherein the vaporizer film is in contact with the wick structure via a base surface, wherein the vaporizer film forms at least one supply channel, via which the at least one first receiving opening can be supplied with the liquid from the wick structure, wherein the vaporizer device comprises a support element comprising an upper side on which the vaporizer film is arranged and a lower side on which the liquid reservoir is arranged, wherein the vaporizer device comprises an opening for receiving the wick structure, and wherein the opening, for receiving the wick structure, fluidically connects the upper side of the support element to the lower side of the support element.

2. The vaporizer device according to claim 1, wherein the at least one supply channel is formed by a fold of the vaporizer film.

3. The vaporizer device according to claim 2, wherein the fold comprises two opposing folding surfaces which are connected to one another via at least one folding edge, wherein at least 20% of the two opposing folding surfaces are aligned parallel to each other.

4. The vaporizer device according to claim 2, wherein a plurality of folds are provided, wherein the folds of the plurality of folds are spaced apart by an intermediate portion of the vaporizer film.

5. The vaporizer device according to claim 1, wherein at least one second receiving opening is provided, which is arranged on the base surface, wherein the at least one second receiving opening can be supplied with the liquid directly via the wick structure.

6. The vaporizer device according to claim 1, wherein at least 20% of an areal extent of the vaporizer film forms the at least one supply channel.

7. The vaporizer device according to claim 1, wherein the at least one supply channel is configured to direct the liquid from the wick structure along a main flow direction to the at least one first receiving opening, wherein the main flow direction encloses an angle between 30° and 150° with the base surface.

8. The vaporizer device according to claim 1, wherein an extension (b) of the at least one supply channel in an orthogonal direction with respect to the base surface corresponds to at least 5 times a height (a) of the vaporizer film.

9. The vaporizer device according to claim 1, wherein the at least one supply channel is dimensioned such that the liquid is transferred from the wick structure to the at least one first receiving opening under action of capillary forces.

10. The vaporizer device according to claim 1, wherein the base surface is a flat surface.

11. A vaporizer device for an inhaler, comprising:

a vaporizer film, wherein the vaporizer film comprises a layer system with a polymer film and at least one metal foil, wherein the at least one metal foil makes surface contact with the polymer film and is designed as a heating element, a liquid reservoir, and a wick structure, which is arranged to supply the vaporizer film with liquid from the liquid reservoir, wherein the vaporizer film comprises at least one first receiving opening for receiving the liquid and at least one dispensing opening for dispensing vaporized liquid, wherein the vaporizer film is in contact with the wick structure via a base surface, wherein the vaporizer film forms at least one supply channel, via which the at least one first receiving opening can be supplied with the liquid from the wick structure, and wherein the base surface is a partial shell surface of a cylinder.

12. The vaporizer device according to claim 11, wherein the wick structure comprises a cylindrical shape with a longitudinal axis, wherein the wick structure is surrounded by the base surface, wherein a main flow direction of the at least one supply channel extends in a radial direction with respect to the longitudinal axis of the wick structure.

13. The vaporizer device according to claim 12, wherein the vaporizer film is surrounded by an outer ring so that a flow channel is formed between the vaporizer film and the outer ring.

14. An inhaler, comprising a vaporizer device according to claim 1.

15. A cartridge for an inhaler, comprising a vaporizer device according to claim 1.

16. A method for operating a vaporizer device, comprising:

providing a vaporizer device according to claim 1, providing an electrical heating voltage to the vaporizer film to generate the vaporized liquid.

17. A method for manufacturing a vaporizer device, wherein the vaporizer device comprises a vaporizer film arranged on a support element, a liquid reservoir, and a wick structure that is arranged to supply the vaporizer film with liquid from the liquid reservoir, wherein the vaporizer film forms at least one supply channel, with which the vaporizer film can be supplied via the wick structure with the liquid to be vaporized from the liquid reservoir, wherein the supply channel is formed by a fold of the vaporizer film, wherein the vaporizer film comprises at least one first receiving opening for receiving the liquid and at least one dispensing opening for dispensing vaporized liquid, wherein the vaporizer film is in contact with the wick structure via a base surface, wherein the vaporizer film is arranged on an upper side of the support element and the liquid reservoir is arranged on a lower side of the support element, wherein the vaporizer device comprises an opening for receiving the wick structure, wherein the opening, for receiving the wick structure, fluidically connects the upper side of the support element to the lower side of the support element, and wherein the method comprises the following steps:

a) providing a base material for manufacture of the vaporizer film comprising a substrate of polyimide with a copper lamination applied thereto on one side;

b) patterning the copper lamination by an etching process so that a copper pattern is formed on the substrate;

c) applying a polyimide cover layer to a side of the substrate with the copper pattern;

d) creating a passage opening through which an upper side of the vaporizer film is fluidically connectable to a lower side of the vaporizer film via a laser;

e) incising a folding edge via a laser so that an incision is formed;

f) folding the vaporizer film along the incised folding edge; and g) joining the folded vaporizer film to the support element.

18. The method according to claim 17, wherein in step b) the following sub-steps are carried out:

b1) applying a photoresist to the copper lamination;

b2) exposure of the photoresist in predefined areas;

b3) developing the photoresist so that remaining photoresist forms a protective layer for the copper lamination in the predefined areas;

b4) applying an etchant to a side with the developed photoresist so that the copper lamination remains on the substrate only in the predefined areas;

b5) removing the remaining photoresist.

19. The method according to claim 17, wherein in step c) applying the polyimide cover layer is carried out by lamination in a vacuum press.

20. The method according to claim 17, wherein in step e) contacting points for supplying the vaporizer film with an electrical heating voltage are additionally exposed via the laser.

21. The method according to claim 17, wherein in step e) the vaporizer film is additionally cut to size for connection to the support element.

* * * * *